US011553730B2

(12) United States Patent
Cameron et al.

(10) Patent No.: US 11,553,730 B2
(45) Date of Patent: Jan. 17, 2023

(54) PRE-FILLED VAPORIZING LIQUID CONTAINER AND PERSONAL VAPORIZING DEVICES FOR USING SUCH CONTAINER

(71) Applicant: LunaTech, LLC, Encino, CA (US)

(72) Inventors: John David Cameron, Encino, CA (US); Jonathan Seamus Blackley, Studio City, CA (US); Mike Elam, Thousand Oaks, CA (US); Alex Gilbert, Thousand Oaks, CA (US); Ravi Sawhney, Thousand Oaks, CA (US); Josh Williams, Studio City, CA (US)

(73) Assignee: Lunatech, LLC, Encino, CA (US)

( * ) Notice: Subject to any disclaimer, the term of this patent is extended or adjusted under 35 U.S.C. 154(b) by 969 days.

(21) Appl. No.: 16/265,593

(22) Filed: Feb. 1, 2019

(65) Prior Publication Data

US 2020/0245692 A1 Aug. 6, 2020

(51) Int. Cl.
*A24B 15/167* (2020.01)
*A61M 11/00* (2006.01)
*B05B 17/06* (2006.01)

(52) U.S. Cl.
CPC ......... *A24B 15/167* (2016.11); *A61M 11/005* (2013.01); *B05B 17/06* (2013.01)

(58) Field of Classification Search
CPC ................................................. A24F 40/00–95
See application file for complete search history.

(56) References Cited

U.S. PATENT DOCUMENTS

| | | | | |
|---|---|---|---|---|
| 4,753,389 A * | 6/1988 | Davis | ...................... | A61L 9/042 239/6 |
| 7,832,410 B2 * | 11/2010 | Hon | ...................... | H05B 1/0291 128/200.14 |
| 8,201,752 B2 * | 6/2012 | Brodbeck | ........... | A01M 1/2077 239/45 |
| 8,393,331 B2 * | 3/2013 | Hon | ...................... | A24B 15/16 131/194 |
| 8,490,628 B2 * | 7/2013 | Hon | ...................... | H05B 3/0014 131/194 |
| 8,893,726 B2 * | 11/2014 | Hon | .................. | A61M 16/0003 131/273 |
| 10,238,144 B2 * | 3/2019 | Hon | .................. | A61M 16/0003 |
| 10,349,682 B2 * | 7/2019 | Hon | ...................... | A24B 15/16 |
| 10,701,982 B2 * | 7/2020 | Hon | ....................... | A24F 40/50 |
| 11,013,870 B2 * | 5/2021 | Hon | ...................... | H05B 1/0291 |
| 2003/0136407 A1 * | 7/2003 | Matsuyama | ......... | A61M 11/005 128/203.16 |
| 2010/0247389 A1 * | 9/2010 | Abate | ...................... | B03C 3/49 422/121 |
| 2010/0300532 A1 * | 12/2010 | Cumpston | ........... | H01L 31/0322 156/322 |

(Continued)

*Primary Examiner* — Gary F Paumen
(74) *Attorney, Agent, or Firm* — Kevin Schraven; Anooj Patel; Hankin Patent Law, APC (57) ABSTRACT

The present disclosure is directed to a pre-filled container configured to store a pre-defined volume of a vaporizable liquid composition. The present disclosure is also directed to personal vaporizing devices for using such containers. In one embodiment, the pre-filled container is configured to provide a vaporizable liquid composition stored therein to an ultrasonic vaporizing component via capillary action for vaporization thereof.

12 Claims, 4 Drawing Sheets

(56) References Cited

U.S. PATENT DOCUMENTS

| | | | | |
|---|---|---|---|---|
| 2015/0374039 A1* | 12/2015 | Zhu | ........................ | H05B 3/03 |
| | | | | 131/329 |
| 2017/0172212 A1* | 6/2017 | Phillips | .................. | A24F 40/42 |
| 2018/0338529 A1* | 11/2018 | Weigensberg | ....... | A61M 11/042 |
| 2019/0030264 A1* | 1/2019 | Herskovic | ............. | A61M 39/10 |
| 2019/0099581 A1* | 4/2019 | Kuzelka | ................ | A61M 16/18 |
| 2020/0222575 A1* | 7/2020 | Rigby | ..................... | F24F 6/12 |

* cited by examiner

PRE-FILLED VAPORIZING LIQUID CONTAINER AND PERSONAL VAPORIZING DEVICES FOR USING SUCH CONTAINER

BACKGROUND

The present disclosure is directed to a pre-filled container configured to store a vaporizable material. The present disclosure is also directed to personal vaporizing devices for using such containers. In one embodiment, the pre-filled container is configured to provide vaporizable material stored therein to a vaporizing component via capillary action.

In recent years, portable electronic vaporizers have gained popularity among users who vaporize herbal extracts to inhale the vapors emitted therefrom. Vaporization is an alternative to burning (smoking) that avoids the inhalation of may irritating toxic and carcinogenic by-products. With little or no smoke produced and generally cooler temperatures than what occurs when material is burned, less material is required to achieve a given level of effect. Hence the irritating and harmful effects of smoking are reduced, as is secondhand smoke.

Many of the battery-powered vaporizers include a reusable battery-containing device portion that connects to one or more cartridges or containers containing the consumable vaporizable material or liquid solution ("E-liquid"). The main ingredients of e-liquids are usually a mixture of propylene glycol, vegetable glycerin, and/or polyethylene glycol, often with differing levels of alcohol mixed with concentrated or extracted flavorings, and a variable concentration of nicotine. In some embodiments, the e-liquid may contain medicinal agents, recreational agents, nutraceuticals, wellness agents, and the like. There is variability in the purity, kinds, and concentrations of ingredients used in the liquids, and significant variability between labelled content and concentration and actual content and concentration.

E-liquid is often sold in bottles, pre-filled disposable containers, or as a kit for consumers to make their own. Components are also available individually and consumers may choose to modify or boost their flavor, nicotine strength, or concentration with various offerings. As a result, consumers will typically prepare e-liquids themselves and will fill containers (or refill used containers) with such prepared e-liquid. Unfortunately, the filling of a container by the consumer often results in uncertainty as to the precise amount of active ingredients contained in the liquid and may introduce contaminants into the liquid and/or container. Furthermore, handling of regulated ingredients and/or those that are potentially dangerous at high concentration when preparing the e-liquid poses a safety concern to the consumer when refilling the containers.

Therefore, it would be desirable to provide pre-filled containers of e-liquid compositions, wherein the e-liquid compositions may contain a multitude of active ingredients, wherein the active ingredients are present in precise amounts as desired for the intended use thereof by a consumer.

SUMMARY

The following presents a simplified overview of the example embodiments in order to provide a basic understanding of some embodiments of the example embodiments. This overview is not an extensive overview of the example embodiments. It is intended to neither identify key or critical elements of the example embodiments nor delineate the scope of the appended claims. Its sole purpose is to present some concepts of the example embodiments in a simplified form as a prelude to the more detailed description that is presented hereinbelow. It is to be understood that both the following general description and the following detailed description are exemplary and explanatory only and are not restrictive.

In accordance with the embodiments disclosed herein, the present disclosure is directed to a pre-filled vaporizing liquid container for use in personal vaporizing devices. The pre-filled container comprises a substantially cylindrically-shaped casing having an external surface and internal surface, the casing having a top end and a bottom end, and a tank defined by the internal surface, the top end of the casing, and the bottom end of the casing, wherein the tank is configured to store a pre-defined volume of a vaporizable liquid composition therein. The pre-filled container further comprises a fluid opening on the top end of the casing, wherein the fluid opening is configured to provide fluid communication of at least a portion of the vaporizable liquid composition stored in the tank and an ultrasonic vaporizing component of an associated personal vaporizer, a removable cap element configured to matingly engage with an upper portion of the casing, wherein the removable cap element, when matingly engaged with the upper portion of the casing, is configured to substantially cover the fluid opening, and an electrical connection on the bottom end of the casing, wherein the electrical connection is configured to be connected to a power supply of the associated personal vaporizer to receive a supply of electric current therefrom. The pre-filled container also includes a porous capillary component extending through the fluid opening in the casing, wherein the porous capillary component is positioned such that a lower region of the porous capillary component will be in contact with at least a portion of the vaporizable liquid composition contained in the tank, and wherein, upon installation into the associated personal vaporizer, an upper region of the porous capillary component will be in contact with an ultrasonic vaporizing component of the associated personal vaporizer. The porous capillary component comprises at least one capillary material having a plurality of capillary pathways, wherein, upon activation of a vaporizing process by the associated personal vaporizer, the at least one capillary material is configured to transport at least a portion of the vaporizable liquid composition stored in the tank toward the ultrasonic vaporizing component of the associated personal vaporizer via at least a portion of the plurality of capillary pathways.

In an embodiment, the casing of the pre-filled container is constructed of at least one material selected from the group consisting of a plastic material, a glass material, a metal material, a carbon fiber material, silicon, a ceramic material, and combinations thereof. In one embodiment, the casing comprises an outer layer and an inner layer, wherein the outer layer is constructed of at least one rigid material, wherein the inner layer defines at least a portion of the tank, wherein the inner layer is constructed of at least one flexible material.

In an embodiment, the tank is constructed of at least one material selected from the group consisting of a plastic material, a glass material, a metal material, a carbon fiber material, silicon, a ceramic material, and combinations thereof. In one embodiment, at least one material used in the construction of the tank is selected based on at least one physical characteristic of the vaporizable liquid compositions stored therein. In a preferred embodiment, the at least one material used in the construction of the tank has minimal interaction with vaporizable liquid composition stored therein.

In another embodiment, the porous capillary component comprises at least one capillary material selected from the group consisting of plastic materials, metals, polymers, natural fibers, synthetic fibers, and combinations thereof. In one embodiment, the at least one capillary material is a fibrous material selected from the group consisting of cellulose, acetate, polyester, bonded polyolefin, polyethylene, polypropylene fibers, nylon fibers, ceramic, and combinations thereof. In a preferred embodiment, the porous capillary component is a porous wick. In yet another embodiment, the porous wick is constructed of a fibrous material selected from the group consisting of cellulose, acetate, polyester, bonded polyolefin, polyethylene, polypropylene fibers, nylon fibers, ceramic, and combinations thereof.

In one embodiment, the removable cap is constructed of at least one material selected from the group consisting of a plastic material, a glass material, a metal material, a carbon fiber material, silicon, a ceramic material, and combinations thereof.

In one embodiment, the vaporizable liquid composition is a water-based vaporizable liquid composition.

In accordance with the embodiments disclosed herein, there is provided a personal vaporizer for using pre-filled vaporizable liquid containers. The personal vaporizer comprises a device processor operable to control the personal vaporizer and a pre-filled container configured to store a pre-defined volume of vaporizable liquid composition. The personal vaporizer further comprises an ultrasonic vaporizing component operatively coupled to the device processor and controlled in part by the device processor, wherein the ultrasonic vaporizing component is in fluid communication with the pre-filled container for receiving a selected amount of vaporizable liquid composition from the container, wherein the ultrasonic vaporizing component comprises an ultrasonic vibration element operable to produce ultrasonic vibrations to vaporize at least a portion of the vaporizable liquid composition received therein. The personal vaporizer also includes a vapor outlet coupled to the ultrasonic vaporizing component and configured to receive vapor generated by the ultrasonic vaporizing component, the vapor outlet operable to expel the generated vapor from the ultrasonic vaporizing component, and a power source operatively coupled to the ultrasonic vaporizing component operable to generate a supply of electric current to be provided to the ultrasonic vaporizing component.

The pre-filled container comprises a substantially cylindrically-shaped casing having an external surface and internal surface, the casing having a top end and a bottom end, and a tank defined by the internal surface, the top end of the casing, and the bottom end of the casing, wherein the tank is configured to store a pre-defined volume of a vaporizable liquid composition therein. The pre-filled container further comprises a fluid opening on the top end of the casing, wherein the fluid opening is configured to provide fluid communication of at least a portion of the vaporizable liquid composition stored in the tank and the ultrasonic vaporizing component, a removable cap element configured to matingly engage with an upper portion of the casing, wherein the removable cap element, when matingly engaged with the upper portion of the casing, is configured to substantially cover the fluid opening, and an electrical connection on the bottom end of the casing, wherein the electrical connection is configured to be connected to the power supply to receive a supply of electric current therefrom. The pre-filled container also includes a porous capillary component extending through the fluid opening in the casing, wherein the porous capillary component is positioned such that a lower region of the porous capillary component will be in contact with at least a portion of the vaporizable liquid composition contained in the tank, wherein, upon installation, an upper region of the porous capillary component will be in contact with the ultrasonic vaporizing component. The porous capillary component comprises at least one capillary material having a plurality of capillary pathways, wherein, upon activation of a vaporizing process, the at least one capillary material is configured to transport at least a portion of the vaporizable liquid composition stored in the tank toward the ultrasonic vaporizing component via at least a portion of the plurality of capillary pathways.

In one embodiment, the casing of the pre-filled container is constructed of at least one material selected from the group consisting of a plastic material, a glass material, a metal material, a carbon fiber material, silicon, a ceramic material, and combinations thereof.

In one embodiment, the tank is constructed of at least one material selected from the group consisting of a plastic material, a glass material, a metal material, a carbon fiber material, silicon, a ceramic material, and combinations thereof. In one embodiment, at least one material used in the construction of the tank is selected based on at least one physical characteristic of the vaporizable liquid compositions stored therein.

In another embodiment, the porous capillary component comprises at least one capillary material selected from the group consisting of plastic materials, metals, polymers, natural fibers, synthetic fibers, and combinations thereof. In one embodiment, the at least one capillary material is a fibrous material selected from the group consisting of cellulose, acetate, polyester, bonded polyolefin, polyethylene, polypropylene fibers, nylon fibers, ceramic, and combinations thereof. In a preferred embodiment, the porous capillary component is a porous wick. In yet another embodiment, the porous wick is constructed of a fibrous material selected from the group consisting of cellulose, acetate, polyester, bonded polyolefin, polyethylene, polypropylene fibers, nylon fibers, ceramic, and combinations thereof.

Still other advantages, embodiments, and features of the subject disclosure will become readily apparent to those of ordinary skill in the art from the following description wherein there is shown and described a preferred embodiment of the present disclosure, simply by way of illustration of one of the best modes best suited to carry out the subject disclosure. As it will be realized, the present disclosure is capable of other different embodiments and its several details are capable of modifications in various obvious embodiments all without departing from, or limiting, the scope herein. Accordingly, the drawings and descriptions will be regarded as illustrative in nature and not as restrictive.

BRIEF DESCRIPTION OF THE DRAWINGS

The drawings are of illustrative embodiments. They do not illustrate all embodiments. Other embodiments may be used in addition or instead. Details which may be apparent or unnecessary may be omitted to save space or for more effective illustration. Some embodiments may be practiced with additional components or steps and/or without all of the components or steps which are illustrated. When the same numeral appears in different drawings, it refers to the same or like components or steps.

DETAILED DESCRIPTION OF THE ILLUSTRATIVE EMBODIMENTS

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

As used herein, the term "by weight," when used in conjunction with a component, unless specially stated to the contrary is based on the total weight of the formulation or composition in which the component is included. For example, if a particular element or component in a composition or article is said to have 8% by weight, it is understood that this percentage is in relation to a total compositional percentage of 100%.

A weight percent of a component, or weight %, or weight percent, or weight % (percent) unless specifically stated to the contrary, is based on the total weight of the formulation or composition in which the component is included.

References in the specification and concluding claims to parts by weight of a particular element or component in a composition or article, denotes the weight relationship between the element or component and any other elements or components in the composition or article for which a part by weight is expressed. Thus, in a composition or a selected portion of a composition containing 2 parts by weight of component X and 5 parts by weight component Y, X and Y are present at a weight ratio of 2:5, and are present in such ratio regardless of whether additional components are contained in the composition.

In the following description, certain terminology is used to describe certain features of one or more embodiments. For purposes of the specification, unless otherwise specified, the term "substantially" refers to the complete or nearly complete extent or degree of an action, characteristic, property, state, structure, item, or result. For example, in one embodiment, an object that is "substantially" located within a housing would mean that the object is either completely within a housing or nearly completely within a housing. The exact allowable degree of deviation from absolute completeness may in some cases depend on the specific context. However, generally speaking, the nearness of completion will be so as to have the same overall result as if absolute and total completion were obtained. The use of "substantially" is also equally applicable when used in a negative connotation to refer to the complete or near complete lack of an action, characteristic, property, state, structure, item, or result.

As used herein, the term "substantially," in, for example, the context "substantially free" refers to a composition having less than about 10% by weight, e.g., less than about 5%, less than about 1%, less than about 0.5% by weight, less than about 0.1% by weight, less than about 0.05% by weight, or less than about 0.01% by weight of the stated material, based on the total weight of the composition.

It is further understood that the term "substantially," when used in reference to a composition, refers to at least about 60% by weight, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% by weight, based on the total weight of the composition, of a specified feature, component, or a combination of the components. It is further understood that if the composition comprises more than one component, the two or more components may be present in any ratio predetermined by one of ordinary skill in the art. For example, and without limitation, the composition comprising substantially water and natural flavor, unless specifically recited, may comprise water and natural flavor in any ratio predetermined by one of ordinary skill in the art.

As used herein, the terms "approximately" and "about" generally refer to a deviance of within 5% of the indicated number or range of numbers. In one embodiment, the term "approximately" and "about", may refer to a deviance of between 0.001-10% from the indicated number or range of numbers.

As used herein, the terms "electronic liquid," "natural-based liquid composition," or "e-liquid" may be used interchangeably and refer to a mixture used in a vapor product, such as an personal vaporizing device. In some embodiments, the personal vaporizing device may include without limitation electronic cigarettes, electronic pipes, electronic cigars, and the like.

Disclosed are components that may be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all embodiments of this application including, but not limited to, steps in disclosed methods. Thus, if there are a variety of additional steps that may be performed it is understood that each of these additional steps may be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware embodiments. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, may be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that may direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, may be implemented by special purpose hardware-based computer systems that perform the specified functions or steps, or combinations of special purpose hardware and computer instructions.

Various embodiments are now described with reference to the drawings. In the following description, for purposes of explanation, numerous specific details are set forth in order to provide a thorough understanding of one or more embodiments. It may be evident, however, that the various embodiments may be practiced without these specific details. In other instances, well-known structures and devices are shown in block diagram form to facilitate describing these embodiments.

In various implementations, there is provided a pre-filled container configured to store a pre-defined volume of a vaporizable liquid composition. The present disclosure is also directed to personal vaporizing devices for using such containers. In one embodiment, the pre-filled container is configured to provide a vaporizable liquid composition stored therein to an ultrasonic vaporizing component via capillary action for vaporization thereof.

In one embodiment, disclosed is personal vaporizing device (e.g., e-cigarette) enabled with a broad range of functionality options and may be configured for use with the pre-filled capillary action vaporizing liquid container. These functionalities are enabled by a microprocessor controller utilized to execute commands for system functionality, along with a memory, transmitter, software, storage, and power system. The personal vaporizing device itself may be outfitted with ultrasonic vaporizing component, cooling element, and a variety of attendant functionality options. Such options include networking and communication services, device monitoring, mixing, cooling, refilling, aromatic, and other distribution functions, external monitoring, testing, powering options, portability, device effects including sound, imaging, light and graphical effects, remote and third-party control, symbiotic characteristics with other devices, and synchronicity among devices.

Figure 1:
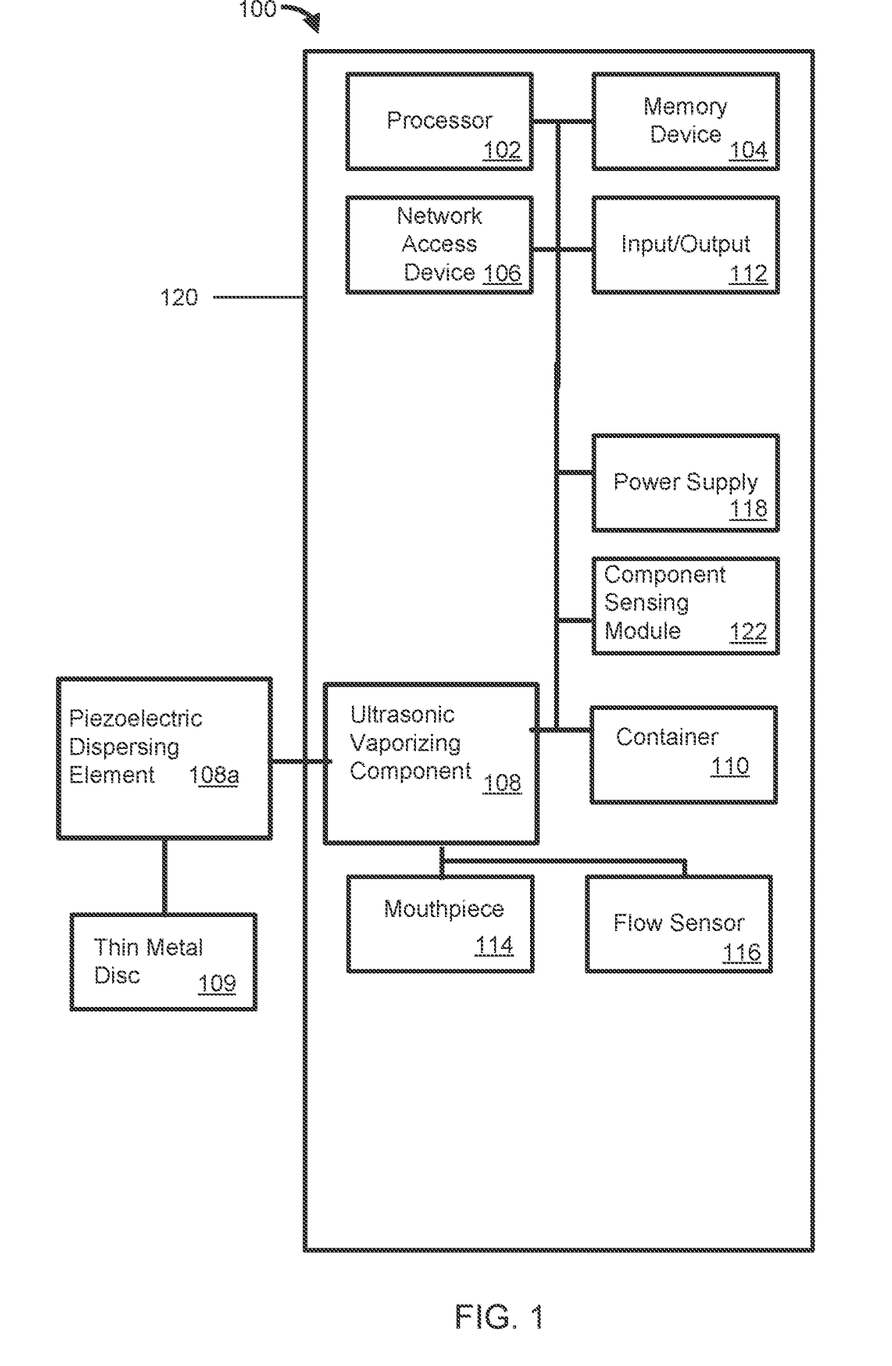
FIG. 1 illustrates block diagrams of one embodiment of personal vaporizing device for use with the pre-filled capillary action vaporizing liquid container according to some embodiments.

FIG. 1 is a block diagram of one embodiment of a personal vaporizing device 100 as described herein. The personal vaporizing device 100 may be, for example, an electronic cigarette, an electronic cigar, an electronic vapor device, a modified vapor device (also known as a mod), a micro-sized electronic vapor device, and the like. The personal vaporizing device 100 may comprise any suitable housing 120 for enclosing and protecting the various components disclosed herein. The personal vaporizing device 100 may comprise a processor 102 operable to control the operation of the personal vaporizing device 100. The processor 102 may be, or may comprise, any suitable microprocessor or microcontroller, for example, a low-power application-specific controller (ASIC) and/or a field programmable gate array (FPGA) designed or programmed specifically for the task of controlling a device as described herein, or a general purpose central processing unit (CPU), for example, one based on 80×86 architecture as designed by Intel™ or AMD™, or a system-on-a-chip as designed by ARM™. The processor 102 may be coupled (e.g., communicatively, operatively, etc.) to auxiliary devices or modules of the personal vaporizing device 100 using a bus or other coupling. The personal vaporizing device 100 may comprise power supply 118. The power supply 118 may comprise one or more batteries and/or other power storage device (e.g., capacitor) and/or a port for connecting to an external power supply. The one or more batteries may be rechargeable. The one or more batteries may comprise a lithium-ion battery (including thin film lithium ion batteries), a lithium-ion polymer battery, a nickel-cadmium battery, a nickel metal hydride battery, a lead-acid battery, super-capacitor, ultra-capacitor, combinations thereof, and the like. For example, an external power supply may supply power to the personal vaporizing device 100 and a battery may store at least a portion of the supplied power.

The personal vaporizing device 100 may comprise a memory device 104 coupled to the processor 102. The memory device 104 may comprise a random-access memory (RAM) configured for storing program instructions and data for execution or processing by the processor 102 during control of the personal vaporizing device 100. When the personal vaporizing device 100 is powered off or in an inactive state, program instructions and data may be stored in a long-term memory, for example, a non-volatile magnetic optical, or electronic memory storage device (not shown). At least one of the RAM or the long-term memory may comprise a non-transitory computer-readable medium storing program instructions that, when executed by the processor 102, cause the personal vaporizing device 100 to perform all or part of one or more methods and/or operations described herein. Program instructions may be written in any suitable high-level language, for example, C, C++, C# or the Java™, and compiled to produce machine-language code for execution by the processor 102 or directly written in machine code.

In one embodiment, the personal vaporizing device 100 may comprise a network access device 106 allowing the personal vaporizing device 100 to be coupled to one or more ancillary devices (not shown) such as via an access point (not shown) of a wireless telephone network, local area network, or other coupling to a wide area network, for example, the Internet. In that regard, the processor 102 may be configured to share data with the one or more ancillary devices via the network access device 106. The shared data may comprise, for example, usage data and/or operational data of the personal vaporizing device 100, a status of the personal vaporizing device 100, a status and/or operating condition of one or more the components of the personal vaporizing device 100, text to be used in a message, a product order, payment information, and/or any other data. Similarly, the processor 102 may be configured to receive control instructions from the one or more ancillary devices via the network access device 106. For example, a configuration of the personal vaporizing device 100, an operation of the personal vaporizing device 100, and/or other settings of the personal vaporizing device 100, may be controlled by the one or more ancillary devices via the network access device 106. For example, an ancillary device may comprise a server that may provide various services and another ancillary device may comprise a smartphone for controlling operation of the personal vaporizing device 100. In some embodiments, the smartphone or another ancillary device may be used as a primary input/output of the personal vaporizing device 100 such that data may be received by the personal vaporizing device 100 from the server, transmitted to the smartphone, and output on a display of the smartphone.

In an embodiment, the personal vaporizing device 100 may also comprise an input/output device 112 coupled to one or more of the processor 102, the network access device 106, the vaporizing component 108, and/or any other electronic component of the personal vaporizing device 100. Input may be received from a user or another device and/or output may be provided to a user or another device via the input/output device 112. The input/output device 112 may comprise any combinations of input and/or output devices such as buttons, knobs, keyboards, touchscreens, displays, light-emitting elements, a speaker, and/or the like. In an embodiment, the input/output device 112 may comprise an interface port (not shown) such as a wired interface, for example a serial port, a Universal Serial Bus (USB) port, an Ethernet port, or other suitable wired connection. The input/output device 112 may comprise a wireless interface (not shown), for example a transceiver using any suitable wireless protocol, for example Wi-Fi (IEEE 802.11), Bluetooth®, infrared, or other wireless standard. For example, the input/output device 112 may communicate with a smartphone via Bluetooth® such that the inputs and outputs of the smartphone may be used by the user to interface with the personal vaporizing device 100. In an embodiment, the input/output device 112 may comprise a user interface. The user interface may comprise at least one of lighted signal lights, gauges, boxes, forms, check marks, avatars, visual images, graphic designs, lists, active calibrations or calculations, 2D interactive fractal designs, 3D fractal designs, 2D and/or 3D representations of vapor devices and other interface system functions.

In an embodiment, the input/output device 112 may comprise a touchscreen interface and/or a biometric interface. For example, the input/output device 112 may include controls that allow the user to interact with and input information and commands to the personal vaporizing device 100. For example, with respect to the embodiments described herein, the input/output device 112 may comprise a touch screen display. User inputs to the touch screen display are processed by, for example, the input/output device 112 and/or the processor 102. The input/output device 112 may also be configured to process new content and communications to the personal vaporizing device 100. The touch screen display may provide controls and menu selections, and process commands and requests. The input/output device 112 and/or the processor 102 may receive and interpret commands and other inputs, interface with the other components of the personal vaporizing device 100 as required. In an embodiment, the touch screen display may enable a user to lock, unlock, or partially unlock or lock, the personal vaporizing device 100. The input/output device 112 may thus display information to a user such as a puff count, an amount of vaporizable material remaining in the containers 110, battery remaining, signal strength, combinations thereof, and the like.

As shown in FIG. 1, in an embodiment, the personal vaporizing device 100 comprises an ultrasonic vaporizing component 108. The ultrasonic vaporizing component 108 is coupled to the pre-filled capillary action vaporizable liquid container 110. The pre-filled container 110 is configured to hold one or vaporizable liquid compositions. The ultrasonic vaporizing component 108 may receive at least portion of the vaporizable liquid composition from the pre-filled container 110 for vaporizing at least a portion of the liquid composition. In another embodiment, the ultrasonic vaporizing component 108 may comprise a magnetic shape memory with an atomizing nozzle or a piezoelectric material.

In a preferred embodiment, the ultrasonic vaporizing component 108 comprises a piezo-mechanical dispersing element 108a. In some embodiments, the piezo-mechanical dispersing element 108a may be charged by power source 118 and may be controlled by processor 102. In one embodiment, the piezo-mechanical dispersing element 108a may comprise a thin metal disc 109 which causes dispersion of the fluid fed into the dispersing element through vibration. Once in contact with the piezo-mechanical dispersing element 108a, the vaporizable liquid composition may be vaporized (e.g., turned into vapor or mist) and the vapor may be dispersed via a system pump and/or a sucking action of the user. In some embodiments, the piezo-mechanical dispersing element 108a may cause dispersion of the vaporizable liquid composition by producing ultrasonic vibrations. An electric field applied to a piezo-mechanical material within the piezo-mechanical dispersing element 108a may cause ultrasonic expansion and contraction of the piezo-mechanical material, resulting in ultrasonic vibrations to the disc. The ultrasonic vibrations may cause the vaporizable liquid composition to disperse, thus forming a vapor or mist from the vaporizable liquid composition.

In some embodiments, the connection between the power supply 118 and the piezo-mechanical dispersing element 108a may be facilitated using one or more conductive coils as a signal generator. The conductive coils may provide an ultrasonic power input to the piezo-mechanical dispersing element 108a. In some embodiments, the piezo-mechanical dispersing element 108a may comprise a piezo-mechanical material that may receive the electric signal transmitted from the power supply 118 through the coils and resulting in vaporization (or atomization) of the vaporizable liquid by producing ultrasonic vibrations.

In one embodiment, the piezo-mechanical dispersing element 108a is suitably comprised of at least one piezoelectric material. In a preferred embodiment, the at least one piezoelectric material is selected from the group of piezoelectric material consisting of natural piezoelectric crystals, synthetic piezoelectric crystals, synthetic piezoelectric ceramics, and combinations thereof.

In an embodiment, input from the input/output device 112 may be used by the processor 102 to cause the ultrasonic vaporizing component 108 to vaporize the vaporizable liquid composition. For example, a user may depress a button, causing the ultrasonic vaporizing component 108 to start vaporizing vaporizable liquid composition. A user may then draw on mouthpiece 114 to inhale the vapor. In various embodiments, the processor 102 may control vapor production and flow to the mouthpiece 114 based on data detected by a flow sensor 116. For example, as a user draws on the mouthpiece 114, the flow sensor 116 may detect the resultant pressure and provide a signal to the processor 102. In response, the processor 102 may cause the ultrasonic vaporizing component 108 to begin vaporizing the vaporizable liquid composition, terminate vaporizing the vaporizable liquid composition, and/or otherwise adjust a rate of vaporization of the vaporizable liquid composition.

Figure 2:
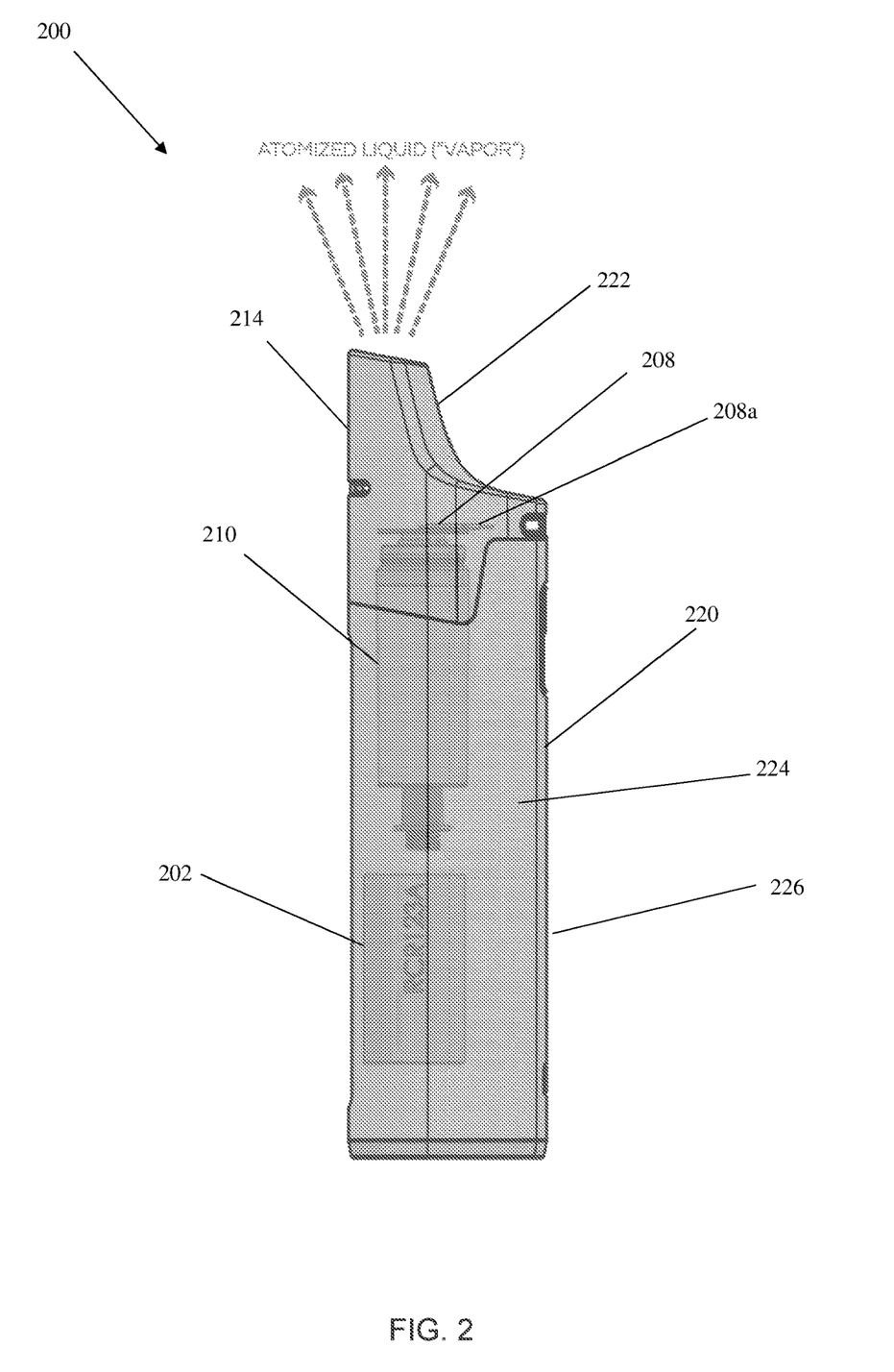
FIG. 2 is an illustration of another embodiment of a personal vaporizing device for use with the pre-filled capillary action vaporizing liquid container according to some embodiments.

FIG. 2 illustrates one embodiment of a personal vaporizer 200. The vaporizer 200 may be, for example, an e-cigarette, an e-cigar, an electronic vapor device, a modified vapor device "mod," a micro-sized personal vaporizing device, and the like. The vaporizer 200 includes a cylindrically-shaped housing 220 having a mouthpiece 214 and an elongated region 222 opposite the mouthpiece 214. The personal vaporizer 200 comprises a processor 202 for controlling the operation of the personal vaporizer 200.

The personal vaporizer 200 further comprises an ultrasonic vaporizing component 208 operatively connected to the processor 202 for controlling the operation of the ultrasonic vaporizing component 208. In a preferred embodiment, the ultrasonic vaporizing component 208 comprises a piezo-mechanical dispersing element 208a. The ultrasonic vaporizing component 208 receives vaporizable liquid composition from container 210 contained within the housing 220. The ultrasonic vibrations produced by the piezo-mechanical dispersing element 208a cause the vaporizable liquid composition to disperse, thus forming a vapor or mist from the vaporizable liquid composition.

The personal vaporizer 200 further includes a display 224 on the cylindrically-shaped housing 220 and operatively connected to the processor 202. The display 224 may be configured to display information associated with the operation of the personal vaporizer 200. The display may be a single LED or may be more complicated, such as but not limited to: a multi-colored LED light (wherein different colors mean different things), a bank or array of LED lights, a 2D LED display, and the like, and combinations thereof. The display 224 may also prompt a user for actions required to operate the personal vaporizer 200.

The personal vaporizer 200 may also comprise a push button control 226 disposed on the elongated region 222 of the cylindrically-shaped housing 222, and operatively connected to the processor 202. The push button control 226 provides a user the ability to control various operations of the personal vaporizer 200 by activating the push button control 226. As an example, such operations may include, but are not limited to, powering the personal vaporizer 200 on and off, activating/deactivating the vaporizing component 208, selecting a mode of operation for the vaporizing component 208, activating a security function of the personal vaporizer 208, and the like, and combinations thereof.

Figure 3A:
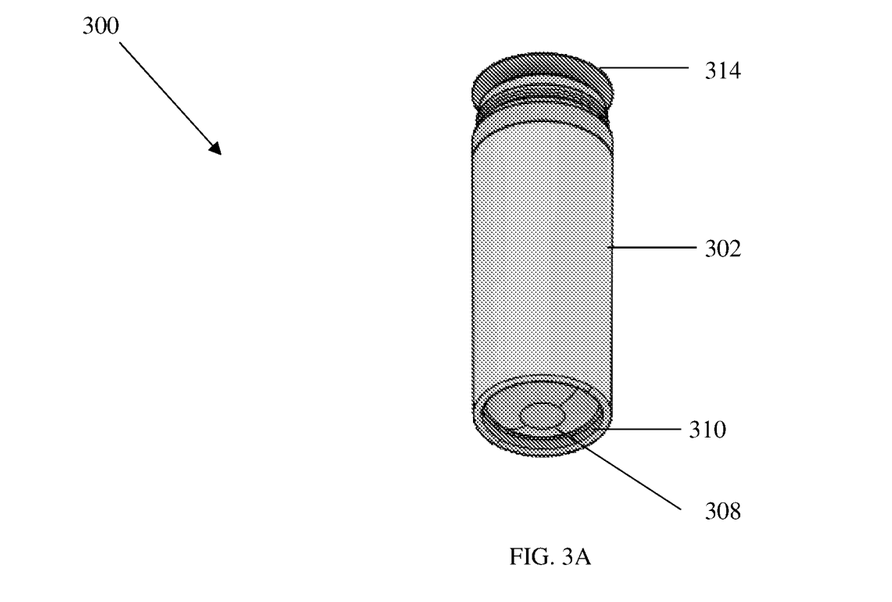
FIGS. 3A and 3B are illustrations of one embodiment of a pre-filled capillary action vaporizing liquid container according to some embodiments.
Figure 3B:
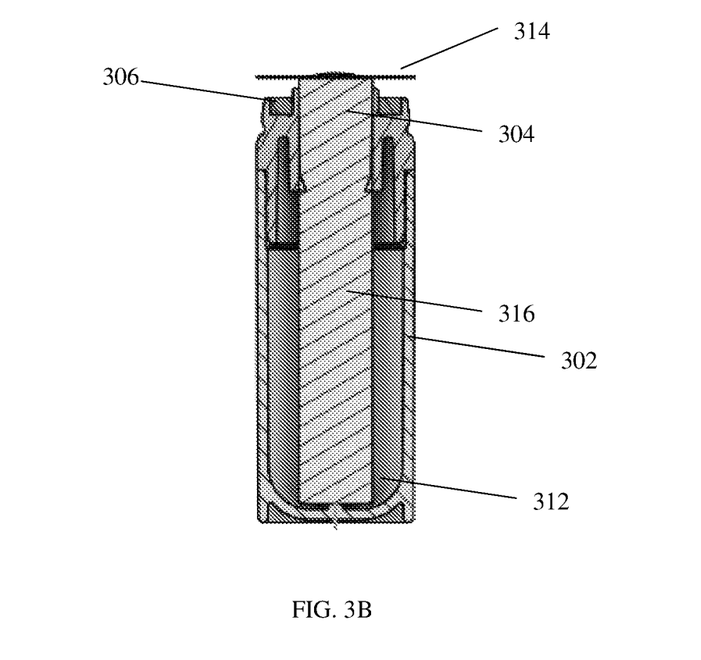

FIGS. 3A and 3B illustrate one embodiment of a pre-filled capillary action vaporizable liquid container 300 for use in a personal vaporizing device, such as personal vaporizing devices 100 and 200. While reference is made to use of the pre-filled cartridge 300 with respect to personal vaporizer 200, it is to be understood that pre-filled container 300, may be used with any suitable personal vaporizing device as is known in the art. The pre-filled container 300 includes an outer casing 302, a fluid opening 304 on the top end 306 of the casing, an electrical conductor 308 on the bottom end 310 of the casing. In a preferred embodiment, the outer casing 302 is substantially cylindrical in shape. The cartridge 300 includes a tank 312 that is defined by the casing 302, the top end 306 of the casing, and the bottom end 310 of the casing. The tank 312 contains a vaporizable liquid composition to be provided to a vaporizing component for vaporization thereof. As shown in FIG. 3, the pre-filled container 300 may further include a cap element 314 positioned on the top end 306 of the casing to protect the fluid opening 304 until such time as the pre-filled container 300 is inserted into the personal vaporizing device for use therein. As shown in FIGS. 3A and 3B, the fluid opening 304 is provided at top end of the casing 306 and is connected to a vaporizing component, such as vaporizing component 208, such that the vaporizable liquid composition is drawn into the ultrasonic vaporizing component 208. The electrical conductor 308 on the bottom end 310 of the casing is connected to a power supply.

The casing 302 of the prefilled container is comprised of any suitable material designed or configured to contain a vaporizable liquid composition therein. The casing 302 may be comprised of one or more materials, including, but not limited to, a plastic material, a glass material, a metal material, a carbon-fiber material, silicon, ceramic material, and combinations thereof. In a preferred embodiment, the casing 302 is comprised of one or more materials that have minimal or no interaction with vaporizable liquid composition contained therein. Examples of suitable plastic materials include, but are not limited to high density polyethylene, polyvinyl chloride, polypropylene, polycarbonate, and combinations thereof. Suitable metal materials include, but are not limited to stainless steel, aluminum, and titanium. Suitable carbon-fiber materials include, but are not limited to, carbon fiber in epoxy resin, and carbon fiber and Kevlar blend in epoxy resin. In a preferred embodiment, the casing 302 may be comprised of a glass material.

In one embodiment, the casing 302 is comprised of a rigid material designed to withstand the operation of a personal vaporing device into which the pre-filled container is inserted for use. In another embodiment, the casing 302 includes an outer layer comprised of a rigid material and an inner layer comprised of soft and/or flexible material. In another embodiment, the casing 302 may be comprised of a rigid material and the tank 312 for holding the vaporizable liquid composition is comprised of a soft and/or flexible material. Suitable flexible materials include, but are not limited to, plastic materials, synthetic and natural rubber materials, carbon fiber materials, and silicon.

The pre-filled container 300 may include a cap element 314 positioned on the top end 306 of the casing to protect the fluid opening 304 until such time as the pre-filled container 300 is inserted into personal vaporizer 200 for use therein. The cap element 314 is configured to matingly engage with the top end 306 of the casing 302 so as to remain affixed thereto until removed by a user of the pre-filled container 300. The cap element 314 may be comprised of one or more materials, including, but not limited to, a plastic material, a glass material, a metal material, a carbon-fiber material, silicon, and combinations thereof. The cap element 314 may be comprised of the same or different material as the casing 302. In a preferred embodiment, the cap element 314 is comprised of one or more materials that have minimal or no interaction with vaporizable liquid composition contained in the pre-filled container 300. Examples of suitable plastic materials include, but are not limited to polypropylene, low-density polypropylene, and combinations thereof. Suitable metal materials include, but are not limited to, stainless steel, aluminum, and titanium. Suitable carbon-fiber materials include, but are not limited to, carbon fiber in epoxy resin, and carbon fiber and Kevlar blend in epoxy resin. In a preferred embodiment, the cap element 314 may be comprised of a stainless steel material with a silicon sealing interface to matingly engage with the casing 302.

As shown in FIGS. 3A and 3B, the pre-filled container 300 and the cap element 314 are configured to be matingly coupled to one another until such time as the cap element 314 is removed therefrom prior to insertion of the pre-filled container 300 into a personal vaporizing device for use therein. For example, the upper portion of the casing 302 may include a threaded fastener and the cap element 314 may comprise a threaded receiver. The threaded fastener and the threaded receiver may be coupled to one another, thereby matingly engaging the cap element 314 to the upper portion of the casing 302. Of course, other types of connection mechanisms that may matingly couple the cap element 314 to the top end 306 and/or the upper portion of the casing 302 are contemplated herein. Such connection mechanisms may include, but are not limited, to snaps, twist caps, push on connections, gasketed connections, quick connection mechanisms, turn lock mechanisms, and the like, and combinations thereof.

The pre-filled container 300 also comprises a tank 312 configured to contain a vaporizable liquid composition to be provided to a vaporizing component, such as ultrasonic vaporizing component 208, for vaporization thereof. The tank 312 is sized and configured to contain pre-defined volume of vaporizable liquid composition at predetermined composition parameters. The tank 312 may be comprised of one or more materials, including, but not limited to, a plastic material, a glass material, a metal material, a carbon-fiber material, ceramic material, silicon, and combinations thereof. The tank 312 may be comprised of the same or different material as the casing 302. In a preferred embodiment, the tank 312 is comprised of one or more materials that have minimal or no interaction with vaporizable liquid composition contained therein. Examples of suitable plastic materials include, but are not limited to high density polyethylene, polyvinyl chloride, polypropylene, polycarbonate, and combinations thereof. Suitable metal materials include, but are not limited to, stainless steel, aluminum, and titanium. Suitable carbon-fiber materials include, but are not limited to, carbon fiber in epoxy resin and carbon fiber and Kevlar blend in epoxy resin. In a preferred embodiment, the tank 312 may be comprised of a glass material.

The vaporizable liquid composition is comprised of any material or combination of materials that may be transformed into a vapor. For example, the vaporizable liquid composition may include water, solvents, active ingredients, ethanol, plant extracts, natural or artificial flavors, and/or vapor formers such as glycerin and propylene glycol.

In some embodiments, the vaporizable liquid composition may include one or more of propylene glycol, glycerin, and combinations. In other embodiments, the vaporizable liquid composition may be comprised of substantially all-natural ingredients. In yet other embodiment, vaporizable liquid composition may be comprised of primarily water. In another embodiment, the vaporizable liquid composition is substantially free of at least one of propylene glycol, vegetable glycerin, and combinations thereof.

In one embodiment, the vaporizable liquid composition may comprise at least one natural flavoring agent comprising a flavor of fruits, berries, spices, herbs, savory flavors, spicy flavors, sweet flavors, plant based flavors, and combinations thereof. In certain embodiments, the natural flavorings may comprise at least one of citrus flavorings, fruit flavorings, berry, spice flavorings, flower flavorings, herbaceous flavorings, vegetable flavorings, savory flavorings, sour flavorings, spicy flavorings, bitter flavorings, and combinations thereof. In yet other embodiments, the natural flavorings may comprise an essence of fruits, vegetables, flowers, spices, alcoholic beverages, or any combinations thereof. In still further embodiments, the vaporizable liquid composition may comprise a manufacturing flavor derived from any natural ingredient that is known to have a pleasant flavor. It is understood that the list of flavorings is not limiting and any flavorings may comprise any component that is known to provide a pleasant taste to the user.

In one embodiment, the vaporizable liquid composition may further comprise at least one natural emulsifier. As one of ordinary skill in the art would readily appreciate, in some embodiments, an emulsifier may be needed to blend ingredients which would otherwise stay immiscible in a liquid due to their chemical composition. In one embodiment, the vaporizable liquid composition is a substantially homogeneous composition. In one embodiment, the natural emulsifier disclosed herein may be any emulsifier capable of stabilizing an emulsion. In a preferred embodiment, the natural emulsifier may comprise a lecithin, a natural starch, a sunflower, or a combination thereof. It is understood that the lecithin may come from various sources. In certain embodiments, the lecithin may be derived from a plant, an animal, or combinations thereof. In one embodiment, the plant-based lecithin may comprise lecithin derived from sunflower, soybeans, rapeseeds, cottonseeds, or any combination thereof. In another embodiment, the animal-based lecithin may comprise lecithin derived from eggs, milk, marine animals, or any combination thereof.

In certain embodiments, the vaporizable liquid composition may comprise at least one supplementary component comprising a medicinal agent or element, a wellness agent or element, a recreational use agent or element, and any combinations of thereof.

In yet other embodiments, the wellness element may comprise chamomile, *Echinacea*, at least one homeopathic remedy, a vitamin supplement, or any combination thereof. In certain exemplary embodiments, the homeopathic remedy may comprise one or more of *Abies Nigra, Carbo vegetablilis, Nux vomica, Robinia pseudoacacia, Arnica Montana, Bryonia, Dulcamara, Pulsatilla, Rhododendron chrysanthum, Rhus tox, Aesculus hippocastanum, Collinsonia Canadensis, Hamamelis virginiana, Phytolacca decandra, Rheum officinale, Dulcamara, Hydrastis Canadensis, Colocynthis, Allium cepa, Apis mellifica, Belladonna Eupatorium perfoliatum, Gelsemium sempervirens, Phytolacca decandra, Pulsatilla. Cimicifuga racemosa, Lycopodium clavatum, Nux moschata, Raphanus sativus, Calendula officinalis, Cineraria maritime, Euphrasia officinalis, Hyoscyamus niger, Nux moschata Passiflora incarnate, Stramonium, Anas barbariae, Arum triphyllum, Belladonna, Phytolacca decandra, Pulsatilla, Spongia tosta, Allium cepa, Ambrosia artemisiaefolia, Sabadilla, Solidago virgaurea, Aconitum napellus, Chelidonium majus, Jequirity, Viburnum opulus, Sanguinaria canadensis, Spigelia anthelmia*, or any combination thereof.

In yet other embodiments, the wellness element may comprise any ancient and modern indigenous people health formulas. In some exemplary embodiments, the formulas may comprise tobacco, sweetgrass, sage, cedar, laurel, caraway, thyme, and the like. In yet other exemplary embodiments, the formulas may include various portions of a plant, for example and without limitation, the formulas may include seeds, berries, roots, leaves, fruits, bark, flowers, or the whole plant.

In certain embodiments, the medicinal element may comprise diabetes medication, respiratory medication, sexual dysfunction remedy, cannabis based medication, or any combination thereof.

In some embodiments, the recreational element may comprise caffeine, nicotine, cannabis-based elements or compounds such as cannabinoids, taurine, salvia, kratum, kava, or any combination thereof. In some embodiments, additional elements may be added to the vaporizable liquid composition. In some embodiments, these elements comprise, for example, one or more additives and/or chemicals found in traditional cigarettes.

All ingredients are mixed in desired percentages by weight, mixed via sonication, and are contained in cartridges that avoid contamination by extractables or leachables. These cartridges are sealed in air-tight, food-safe containers until use and packaged to prevent direct exposure to UV rays. Storage instructions, appropriate fluids, and expiration dates are printed on the packaging to instruct distributors, retailers, and users accordingly.

In operation, when ultrasonic vaporizing component 208 of the personal vaporizer 200 is activated, the vaporizable liquid composition is withdrawn from the pre-filled container 300 and transported to the ultrasonic vaporizing component 208, wherein the liquid composition is vaporized to generate vapor therefrom. In one embodiment, pre-filled container 300 comprises a capillary material 316 for transporting the vaporizable liquid composition from the pre-filled container 300 to the ultrasonic vaporizing component 208 by capillary action. The capillary material 316 provides capillary pathways with which to transport the vaporizable liquid composition from the tank 312 to the ultrasonic vaporizing component 208 at a rate to replace liquid vaporized by the ultrasonic vaporizing component 208 during operation thereof.

The capillary material 316 may comprise any suitable material or combination of material which is able to convey the vaporizable liquid composition from the tank 312 towards the ultrasonic vaporizing component 208. In a preferred embodiment, the capillary material should be comprised of one or more materials that have minimal or no interaction with vaporizable liquid composition contained therein. The capillary material 316 may comprise a porous material and/or may have a fibrous or spongy structure. The capillary material 316 preferably comprises a bundle of capillaries. The structure of the capillary material 316 forms a plurality of small bores or tubes through which the vaporizable liquid composition may be transported from the tank 312 towards the ultrasonic vaporizing component 208. The particular preferred capillary material 316 will depend on the physical properties of the vaporizable liquid composition contained in the pre-filled container 300. Examples of suitable capillary material includes, but is not limited to, sponge or foam material, ceramic- or graphite-based materials in the form of fibers or sintered powders, foamed metal or plastic material, a fibrous material, for example made of spun or extruded fibers, such as cellulose, acetate, polyester, or bonded polyolefin, polyethylene, polypropylene fibers, nylon fibers or ceramic. The capillary material may have any suitable capillarity so as to be used with different liquid physical properties. The liquid physical properties include, but are not limited to, viscosity, surface tension, density, thermal conductivity, boiling point, and vapor pressure, which allow the liquid to be transported through the capillary material. The material and pore size of the capillary material is optimized for the surface tension of the fluid contained in the container, as capillary action occurs when the adhesion to the surface material is stronger than the cohesive force between the fluid's molecules.

In one embodiment, the capillary material 316 may be a porous wick which extends from within the tank 312 to external to the casing 302, such that porous wick may be in contact with the ultrasonic vaporizing component 208. The porous wick may be any appropriate material, including, but not limited to, woven, braided, fibrous, and knitted materials. The porous wick may be any appropriate material, including plastic materials, metals, polymers, natural fibers (wool, cotton, corn fiber, and the like), synthetic fibers, or combinations thereof. The porous wick provides a capillary pathway for the liquid composition within the tank 312 through and into the porous wick. In one embodiment, the capillary pathway is generally large enough to permit wicking of sufficient vaporizable liquid composition to replace vaporized liquid transferred from the tank 312 by capillary action (wicking) during using of the personal vaporizer 200, but small enough to prevent leakage of the vaporizable liquid composition during normal operation.

Figure 4:
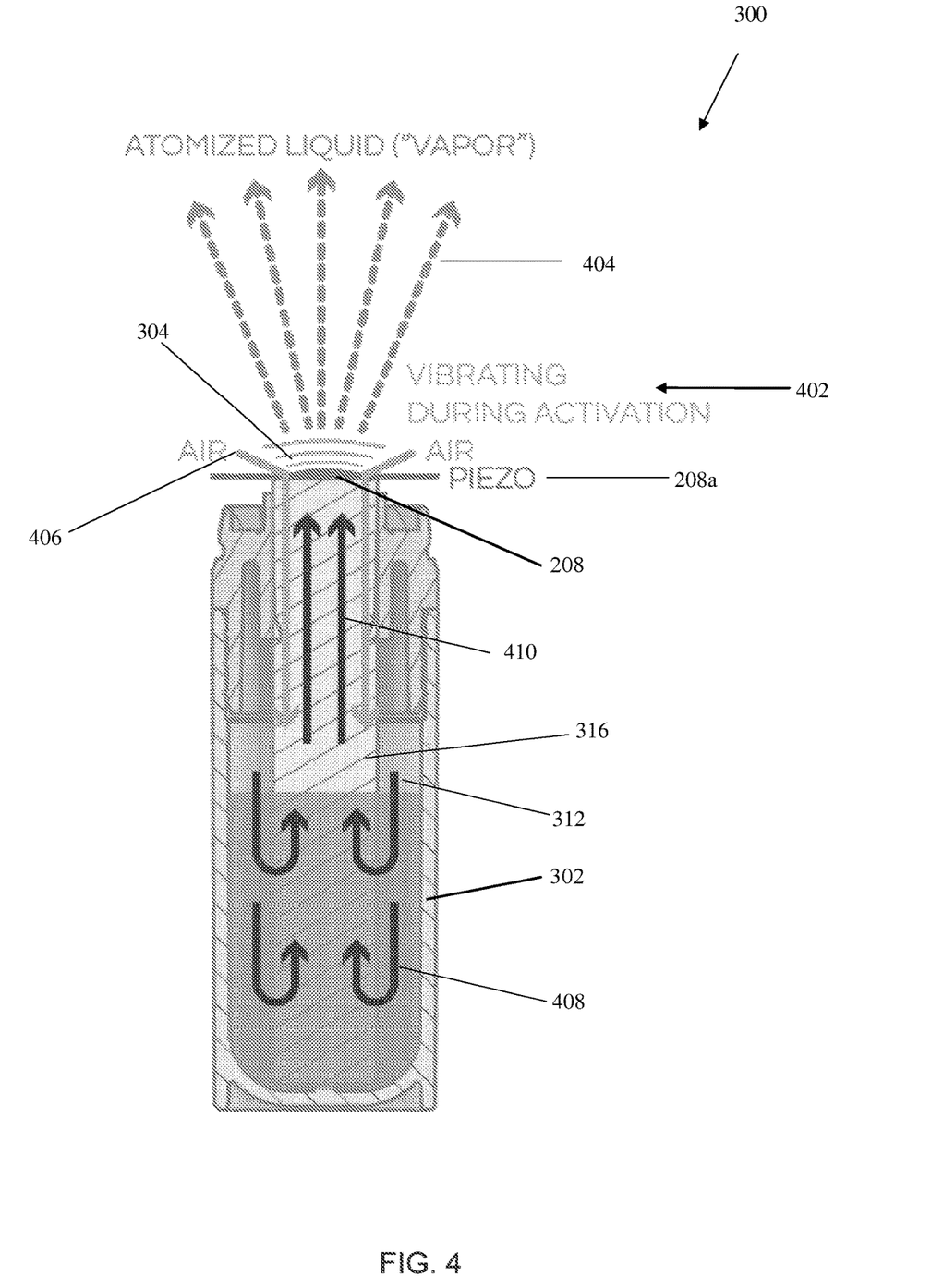
FIG. 4 is an illustration of another embodiment of a pre-filled capillary action vaporizing liquid container according to some embodiments.

FIG. 4 illustrates one embodiment of a capillary material 316, such as a porous wick, transporting the vaporizable liquid composition from the pre-filled container 300 to the ultrasonic vaporizing component 208 by capillary action. In operation, the personal vaporizer 200 may receive an activation signal to commence the vaporization process. Upon activation of the ultrasonic vaporizing component 208, an electric field is applied to the piezo-mechanical dispersing element 208a to create ultrasonic vibrations within the piezo-mechanical dispersing element 208a as shown at 402. The ultrasonic vibrations generate a Rayleigh wave on the surface of the piezo-mechanical dispersing element 208a. As a result, the vaporizable liquid composition in contact with the piezo-mechanical dispersing element 208a disperses, forming a vapor or mist from the vaporizable liquid composition as shown by the vapor dispersion arrows 404. As the vaporizable liquid composition is dispersed, a partial vacuum is created in the cartridge 300, which draws in air around the piezo-mechanical dispersing element 208*a*, as shown by the directional arrows 406. This results in positive pressure on the vaporizable liquid composition, which draws more of the liquid composition into the capillary material 316, as shown by the directional arrows 408. Capillary action then moves the vaporizable liquid composition through the capillary material 316 towards the piezo-mechanical dispersing element 208*a*, as shown by directional arrows 410. The process continues to disperse the atomized liquid composition until the capillary action holding the liquid composition in the capillary material 316 is sufficiently greater than the pressure moving it upward towards the piezo-mechanical dispersing element 208*a*.

In view of the exemplary systems described herein, methodologies that may be implemented in accordance with the disclosed subject matter have been described with reference to several flow diagrams. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described herein. Additionally, it should be further appreciated that the methodologies disclosed herein are capable of being stored on an article of manufacture to facilitate transporting and transferring such methodologies to computers.

Those of ordinary skill in the relevant art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

As used in this application, the terms "component," "module," "system," and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server may be a component. One or more components may reside within a process and/or thread of execution and a component may be localized on one computer and/or distributed between two or more computers.

As used herein, a "vapor" includes mixtures of a carrier gas or gaseous mixture (for example, air) with any one or more of a dissolved gas, suspended solid particles, or suspended liquid droplets, wherein a substantial fraction of the particles or droplets if present are characterized by an average diameter of not greater than three microns. As used herein, an "aerosol" has the same meaning as "vapor," except for requiring the presence of at least one of particles or droplets. A substantial fraction means 10% or greater; however, it should be appreciated that higher fractions of small (<3 micron) particles or droplets may be desirable, up to and including 100%. It should further be appreciated that, to simulate smoke, average particle or droplet size may be less than three microns, for example, may be less than one micron with particles or droplets distributed in the range of 0.01 to 1 micron. A vaporizer may include any device or assembly that produces a vapor or aerosol from a carrier gas or gaseous mixture and at least one vaporizable material. An aerosolizer is a species of vaporizer, and as such is included in the meaning of vaporizer as used herein, except where specifically disclaimed.

Various embodiments presented in terms of systems may comprise a number of components, modules, and the like. It is to be understood and appreciated that the various systems may include additional components, modules, etc. and/or may not include all of the components, modules, etc. discussed in connection with the figures. A combination of these approaches may also be used.

In addition, the various illustrative logical blocks, modules, and circuits described in connection with certain embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, system-on-a-chip, or state machine. A processor may also be implemented as a combination of computing devices, e.g., a combination of a DSP and a microprocessor, a plurality of microprocessors, one or more microprocessors in conjunction with a DSP core, or any other such configuration.

Operational embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, a DVD disk, or any other form of storage medium known in the art. An exemplary storage medium is coupled to the processor such the processor may read information from, and write information to, the storage medium. In the alternative, the storage medium may be integral to the processor. The processor and the storage medium may reside in an ASIC or may reside as discrete components in another device.

Furthermore, the one or more versions may be implemented as a method, apparatus, or article of manufacture using standard programming and/or engineering techniques to produce software, firmware, hardware, or any combination thereof to control a computer to implement the disclosed embodiments. Non-transitory computer readable media may include but are not limited to magnetic storage devices (e.g., hard disk, floppy disk, magnetic strips), optical disks (e.g., compact disk (CD), digital versatile disk (DVD)), smart cards, and flash memory devices (e.g., card, stick). Those skilled in the art will recognize many modifications may be made to this configuration without departing from the scope of the disclosed embodiments.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those of ordinary skill in the art that various modifications and variations may be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A pre-filled vaporizable liquid container for use with a personal vaporizer, comprising:
a substantially cylindrically-shaped casing having an external surface and internal surface, the casing having a top end and a bottom end;
a tank defined by the internal surface, the top end of the casing, and the bottom end of the casing, wherein the tank is configured to store a pre-defined volume of a vaporizable liquid composition therein;
a fluid opening on the top end of the casing, wherein the fluid opening is configured to provide fluid communication of at least a portion of the vaporizable liquid composition stored in the tank to an ultrasonic vaporizing component of an associated personal vaporizer;
a removable cap element configured to matingly engage with an upper portion of the casing, wherein the removable cap element, when matingly engaged with the upper portion of the casing, is configured to substantially cover the fluid opening, and wherein the removable cap element is comprised of a stainless steel material with a silicon sealing interface to matingly engage with said upper portion of the casing; and
a porous capillary component extending through the fluid opening in the casing, wherein the porous capillary component is positioned such that a lower region of the porous capillary component will be in contact with at least a portion of the vaporizable liquid composition contained in the tank, wherein, upon installation into the associated personal vaporizer, an upper region of the porous capillary component will be in contact with an ultrasonic vaporizing component of the associated personal vaporizer, wherein the porous capillary component comprises at least one capillary material having a plurality of capillary pathways, wherein, upon activation of a vaporizing process by the associated personal vaporizer, the at least one capillary material is configured to transport at least a portion of the vaporizable liquid composition stored in the tank toward the ultrasonic vaporizing component of the associated personal vaporizer via at least a portion of the plurality of capillary pathways.

2. The pre-filled container of claim 1, wherein the casing is constructed of at least one material selected from the group consisting of a plastic material, a glass material, a metal material, a carbon fiber material, silicon, a ceramic material, and combinations thereof.

3. The pre-filled container of claim 1, wherein the casing comprises an outer layer and an inner layer, wherein the outer layer is constructed of at least one rigid material, wherein the inner layer defines at least a portion of the tank, wherein the inner layer is constructed of at least one flexible material.

4. The pre-filled container of claim 1, wherein the tank is constructed of at least one material selected from the group consisting of a plastic material, a glass material, a metal material, a carbon fiber material, silicon, a ceramic material, and combinations thereof.

5. The pre-filled container of claim 4, wherein at least one material used in the construction of the tank is selected based on at least one physical characteristic of the vaporizable liquid compositions stored therein.

6. The pre-filled container of claim 1, further comprising an electrical connection on the bottom end of the casing, wherein the electrical connection is configured to be connected to a power supply of the associated personal vaporizer to receive a supply of electric current therefrom.

7. The pre-filled container of claim 1, wherein the porous capillary component comprises at least one capillary material selected from the group consisting of plastic materials, metals, polymers, natural fibers, synthetic fibers, and combinations thereof.

8. The pre-filled container of claim 7, wherein the at least one capillary material is a fibrous material selected from the group consisting of cellulose, acetate, polyester, bonded polyolefin, polyethylene, polypropylene fibers, nylon fibers, ceramic, and combinations thereof.

9. The pre-filled container of claim 1, wherein the porous capillary component is a porous wick.

10. The pre-filled container of claim 9, wherein the porous wick is constructed of a fibrous material selected from the group consisting of cellulose, acetate, polyester, bonded polyolefin, polyethylene, polypropylene fibers, nylon fibers, ceramic, and combinations thereof.

11. The pre-filled container of claim 1, wherein the removable cap is constructed of at least one material selected from the group consisting of a plastic material, a glass material, a metal material, a carbon fiber material, silicon, a ceramic material, and combinations thereof.

12. The pre-filled container of claim 1, wherein the vaporizable liquid composition is a water-based vaporizable liquid composition.

* * * * *